(12) United States Patent
Holland et al.

(10) Patent No.: US 6,547,752 B2
(45) Date of Patent: Apr. 15, 2003

(54) ORTHOTIC DEVICE FOR TREATING CONTRACTURES OF EITHER HAND

(75) Inventors: Marlan J. Holland, Atascadero, CA (US); John P. Kenney, Laguna Niguel, CA (US)

(73) Assignee: Soft Wear, Inc., Incline Village, NV (US)

( * ) Notice: Subject to any disclaimer, the term of this patent is extended or adjusted under 35 U.S.C. 154(b) by 10 days.

(21) Appl. No.: 09/746,920

(22) Filed: Dec. 23, 2000

(65) Prior Publication Data

US 2002/0082538 A1 Jun. 27, 2002

(51) Int. Cl.[7] .................................................. A61F 5/00
(52) U.S. Cl. ........................... 602/20; 602/21; 128/878; 128/879
(58) Field of Search ...................... 602/5, 6, 12, 20–22, 602/62, 64; 128/878–880

(56) References Cited

U.S. PATENT DOCUMENTS

| | | | | |
|---|---|---|---|---|
| 4,928,677 A | * | 5/1990 | Barber | 2/11 |
| 5,248,292 A | * | 9/1993 | Holland | 602/20 |
| 5,417,645 A | * | 5/1995 | Lemmen | 144/162.1 |
| 5,733,249 A | * | 3/1998 | Katzin et al. | 602/21 |
| 5,891,068 A | | 4/1999 | Kenney | |
| 5,916,186 A | * | 6/1999 | Turto et al. | 602/12 |
| 6,165,148 A | * | 12/2000 | Carr-Stock | 128/878 |

* cited by examiner

Primary Examiner—Michael A. Brown
Assistant Examiner—Quang D Thanh
(74) Attorney, Agent, or Firm—Howard R. Lambert

(57) ABSTRACT

A universal hand orthotic device is provided for treating contractures in a patient's left or right hand. The device comprises a bendable metal splint having a central, wrist support region with a hand support region projecting sidewardly from an upper end of the central region. Ears projecting to opposite sides of a lower end of the splint central region are bendable to fit the splint at least partially around a patient's left or right wrist according to intended use of the device. The splint is installed between relatively soft plastic foam pads. The padded splint is received into a padded mitt at least hand regions of which are formed of a smooth, non-irritating fabric. Straps attached to the mitt enable its releasable attachment to a patient's wrist and hand. A plurality of resilient cylinders of increasing diameters detachably attach to a mitt finger-grip region.

26 Claims, 4 Drawing Sheets

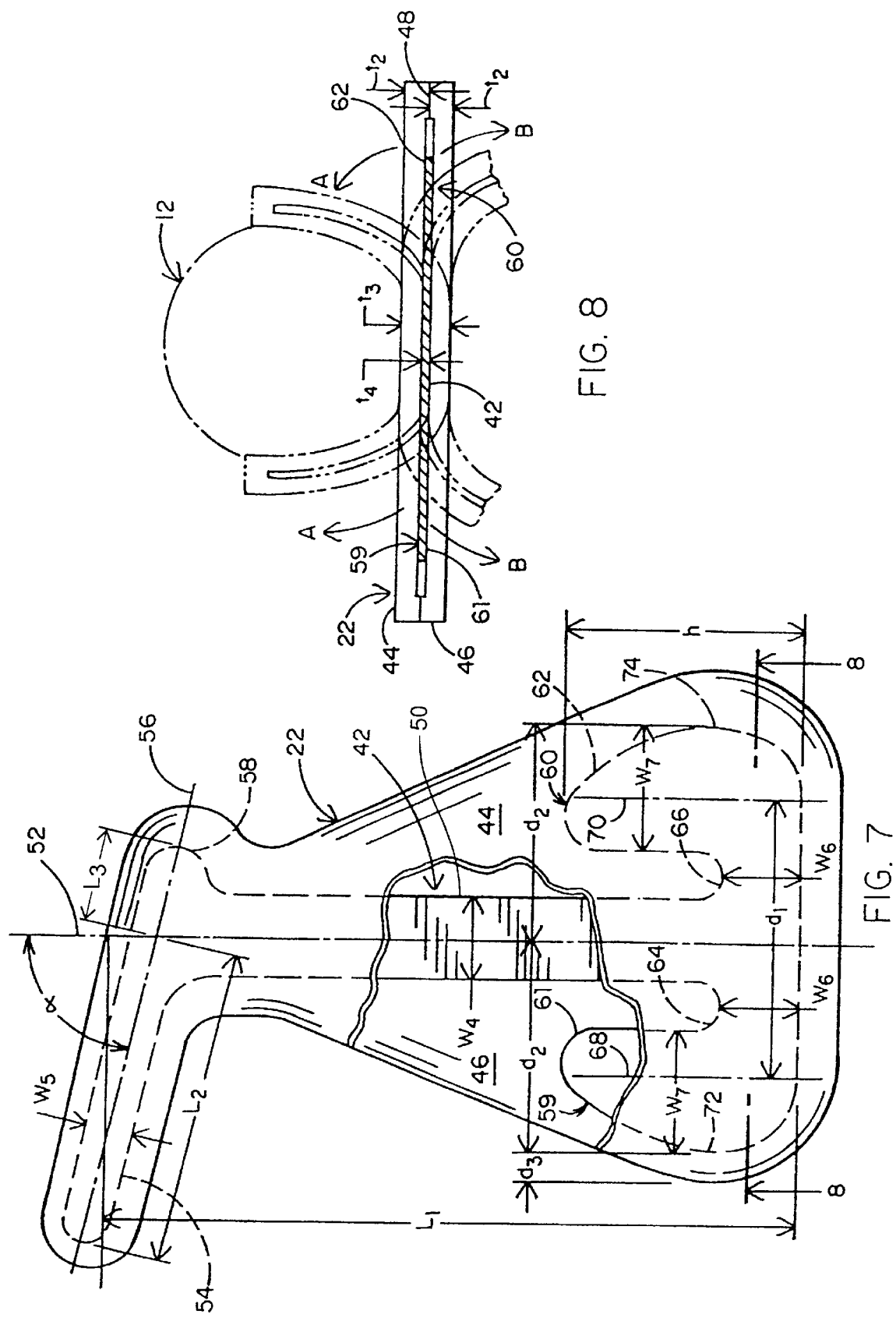

ORTHOTIC DEVICE FOR TREATING CONTRACTURES OF EITHER HAND

BACKGROUND OF THE INVENTION

1. Field of the Invention

The present invention relates generally to the field of orthotic devices and appliances; more particularly to orthotic devices and appliances useful for restoring movement to a connective joint of a mammalian body; and still more particularly to orthotic devices and appliances used to reverse contractures due to immobility and neurological dysfunction of a human patient's hand and fingers.

2. Background Discussion

Webster's New Collegiate Dictionary defines "orthotics" as "a branch of mechanical and medical science that deals with the support and bracing of weak or ineffective joints or muscles."

Orthotic devices and appliances, commonly referred to just as "orthotics" (in spite of the broader dictionary definition of orthotics), have been utilized for many years by physical therapists, occupational therapists, and certified orthotic fitters to assist in the rehabilitation of loss of range of motion (LROM) of patients' joints and associated limbs or adjacent skeletal parts of the patients' body.

Orthotics, as well as splints, have been designed both to maintain and to restore the range of bodily motion due to LROM. Such loss of range of motion may, for example, be caused by traumatic injury, joint or limb surgery, contracture due to immobilization caused by neuromuscular disorders (e.g., stoke and closed head injury) and other disease processes that significantly limit a patients ability to use a joint for normal activities of daily living (ADL).

Two fundamentally different types of contractures exist which clinically should have two different treatment protocols. The difference in these two types of contractures is the basis for the clinical techniques and design of the orthotics of the present invention that will be described below.

A first one of these two fundamentally different types of contracture may be defined as a fixed, high resistance of muscle to passive stretch resulting from fibrosis of the muscles and joints, or from disorders of the muscle fiber resulting in LROM, for example, of a patient's hand and fingers. In this regard, Webster's Dictionary defines "contracture" as "a permanent shortening (as of muscle, tendon and scar tissue) producing deformity or distortion."

This first type of contracture is usually due to trauma, injury, or surgical intervention affecting the joint, as may be typical of sports injuries and the treatment thereof. As the injured tissue heals, edema, post trauma or surgically affected tissue regeneration and other natural healing processes result in fusing together of what were, prior to the trauma, separate, pristine connective tissues, that is, the collagen fiber matrix, capable of easily gliding over one another, as is needed for normal joint movement and related muscle elongation.

However, post-trauma, this collagen fiber matrix becomes random and irregular, and neither elongates nor stretches compared to non-traumatized collagen fibers. This fusing-together or adhesion of connective tissue structures (e.g., ligaments, tendons, synovial membrane, fascia and fibrous joint capsules) is the result of the tissues being invaded by developing undifferentiated scar between adjacent tissue, thereby diminishing or preventing the mutual gliding after early healing of the trauma or post-surgical trauma has been accomplished.

This post-trauma matrix condition, as well as the above-mentioned normal matrix condition, is depicted and discussed in U.S. Pat. Nos. 5,891,068 and 6,001,074 to John P. Kinney, one of the present inventors. These two patents are hereby incorporated in their entirety in this application.

Such fusing together of connective tissue is a leading cause of lags (a non-specific indictment of the motor system's failure to move the affected joint through the full available passive range) relating to tendon gliding, depending on their strategic placement in reference to structures crossing the joint.

With limited mobility and associated extensor muscle atrophy, combined with the formation of adhesions and scar tissue in the form of a significantly increased number of joined fiber matrix junctions, the muscle fibers become shortened.

The restoration of full range of motion where fibrosis of the muscle fiber with scar tissue and adhesions are present requires that the adhesions and scar tissue or fused fiber matrix junctions be "worked through" or broken to restore normal functional elongation or stretch.

The term "no pain, no gain" (of increased range of motion) is associated with the process of breaking through joined or fused fiber matrix junctions to restore full elongation of the connective tissue, tendons and muscles associated with the trauma-affected joint.

Heretofore known orthotics are primarily designed to treat this first type of contracture, but have also been used to treat contractures caused by immobility and neurological dysfunction (described below). However, such orthotic devices are not, as far as is known by the present inventor, best suited for such additional purpose.

The second and very different type of contracture results from joint immobility—not joint-related trauma or surgical repair of a joint. Contracture resulting from immobility is simply a shortening and thickening of the connective tissue, tendons and muscles that restrict the ROM of a joint. In such situations, the muscle fibers still retain their original uniform shape and there are no adhesions or scar tissue or significantly increased joined fiber matrix junctions to break through in order to restore full range of motion.

In contrast to trauma-caused contractures, contractures due to immobility do not need a "no pain, no gain" approach to restore the normal range of motion, and, in fact, such an approach can actually do more harm than good. As mentioned above, the collagen fibers of a contracture due to immobility are simply shorter and thicker, and will respond to appropriate stretching techniques and motion of the joint to restore LROM. The stretching technique usually used for contractures caused by immobility is Range Of Motion (ROM) Therapy and the use of Low-Load Protracted Stretch/Stress (LLPS) or "extended stretch" static or dynamic orthotic devices.

According to authors Kenneth R. Flowers and Susan L. Michlovitz in their article titled "ASSESSMENT AND MANAGEMENT OF LOSS OF MOTION IN ORTHOPEDIC DYSFUNCTION" (published in Postgraduate Advances in PHYSICAL THERAPY, American Physical Therapy Association, 1988 II–VIII), Total End Range Time (TERT) in conjunction with LLPS is the key to restoring full ROM.

All contractures, whether caused by injury, surgery, or immobility, limit range of motion of the affected joint and make simple activities of daily living, such as eating and self-dressing, more difficult, if not impossible. Moderate to severe contractures can be debilitating, and can leave afflicted individuals unable to care for themselves in the most basic daily living tasks. Even mild contractures due to immobility can progress to severe contractures if proper intervention is not prescribed and implemented so long as the immobility continues. The main function of my new and more effective orthotic devices is to treat contracture due to immobility-not trauma related to surgery or injury.

The above-cited Kenney patents disclose a variety of orthotic devices particularly useful for treating contractures of arms, hands, legs, feet, neck and back due to immobility.

The main function of my new and more effective orthotic devices is to treat contracture due to immobility-not trauma related to surgery or injury. In this regard, contractures and other hazards of immobility are one of the ten current highest health care costs in America that are totally preventable. This puts the health risks associated with immobility in the same category as cigarette smoking, alcohol and drug abuse, and automobile accidents in financial impact on American health care costs.

Recent managed care cost reimbursement decisions have, however, drastically limited professional therapeutic treatment for conditions, including immobility related conditions, which would otherwise be expected to respond favorably to professional rehabilitation therapy. Such managed care decisions have not only very substantially reduced the overall lengths of reimbursable therapy times for all types of patient conditions requiring professional therapeutic rehabilitation treatment, but have also put cost-reduction pressure on the manufacture and sale of therapeutic equipment and orthotic devices and appliances.

For these and other reasons, the present inventors have devised an improved orthotic device for treatment of contractures of the hand and fingers that is readily adapted for use with either a left hand or a right hand. The main function of our improved orthotic devices is to treat contracture due to immobility—not due to trauma related to surgery or injury. Thus our improved orthotic device is uniquely appropriate for contractures due to immobility where neurological dysfunction is present in a patient's hand and fingers.

Our universal hand orthotic device, easily adapted for use with most sizes of either a left hand or a right hand, will importantly reduce costly inventory requirements for therapeutic facilities and is expected to result in cost savings for patients requiring such devices and for their associated health care provider.

SUMMARY OF THE INVENTION

In accordance with the present invention, there is provided a universal orthotic device for treating contractures of either a patient's left hand or right hand. As such, the device may be considered an ambidextrous hand orthotic device. The universal hand orthotic device of the present invention comprises a manually bendable, thin metal splint element having an elongate central, wrist support region. An elongate hand support region extends sidewardly from an upper end of the central region at an angle, $\alpha$, of between about 75 and about 80 degrees, and more preferably about 77 degrees, relative to a longitudinal axis of the central region.

A first ear projects to one side of a lower end of the splint element central region and a second ear projects to an opposite side of the lower end of the central region, the first and second ears being manually bendable relative to the central region to enable the splint element to fit at least partially around either a patient's left wrist or a patient's right wrist according to the intended use of the device.

The first and second ears each include an enlarged outboard end region joined to the central region by a smaller, necked-down region having a width parallel to said central region longitudinal axis of between about 0.5 and about 0.75 inches.

The splint element is substantially planar in shape before any bending of the first and second ears, and is preferably constructed from a relatively soft aluminum alloy having a sheet thickness of between about 0.040 and about 0.0938 inches.

It is preferred that the central region of the splint element have a width of about one inch and the hand support region have a width of about 0.5 inches. Each of the first and second ears preferably extend about 2.25 inches from the longitudinal axis of the central region. The splint element has a preferred overall height between about 7 and about 7.5 inches along the central region longitudinal axis.

The splint element is preferably disposed between first and second, relatively soft pads of a closed cell plastic material. The pads are shaped to generally follow the shape of the splint element and are cemented together around the splint element to form a padded splint assembly having a preferred thickness of about 0.375 inches.

The device includes a padded fabric mitt configured for receiving the splint element, the mitt including closure means for retaining the splint element in the mitt. At least one strap, preferably a plurality of straps, is attached to the mitt for enabling the releasable attachment of the mitt to a patient's wrist and hand. Claim 17. The exterior of at least hand regions of the padded mitt are formed of a smooth, non skin irritating fabric. Preferably further included as part of the device is at least one resilient cylinder configured for detachable attachment to a finger-grip region of the mitt.

A universal hand orthotic device for treating contractures in either of a patient's left hand or right hand thus comprises a manually bendable splint element constructed from a relatively soft aluminum alloy having a sheet thickness of between about 0.040 and about 0.0938 inches. The splint element has an elongate central, wrist support region with an elongate hand support region projecting sidewardly from an upper end of the central region at an angle between about 75 and about 80 degrees, relative to a longitudinal axis of the central region, a first ear projecting to one side of a lower end of said central region, and a second ear projecting to an opposite side of the lower end of said central region. The first and second ears being manually bendable relative to the central region to configure the splint element to fit at least partially around either a patient's left wrist or a patient's right wrist according to the intended use of said device. The first and second ears each include an enlarged outboard end region joined to the central region by a necked-down region having a width parallel to the central region longitudinal axis of between about 0.5 and about 0.75 inches.

The splint element has an overall height between about 7 inches and about 7.5 inches along said central region longitudinal axis, wherein said splint element central region has a width of about one inch, wherein said splint element hand support region has a width of about 0.5 inches and wherein each of said first and second ears extend about 2.25 inches from the longitudinal axis of said central region.

First and second, relatively soft flat pads constructed from a closed cell plastic foam material having a thickness of at least about 0.188 inches are included, the splint element being disposed between the first and second pads to thereby form a padded splint assembly. The first and second pads are contoured to generally follow the shape of the splint element and are cemented together around said splint element.

A padded fabric mitt is included for receiving the padded splint assembly the mitt including closure means for retaining the padded splint assembly in the mitt. The exterior of at least hand regions of said mitt are formed of a smooth, non skin irritating fabric. At least two straps are attached to the fabric mitt for enabling the releasable attachment of the mitt to a patient's wrist and hand.

Included is a plurality of resilient cylinders of increasing diameters configured for detachable attachment to a finger-grip region of the mitt.

BRIEF DESCRIPTION OF THE DRAWINGS

The present invention may be more readily understood when taken in conjunction with the accompanying drawings in which:

FIG. 7 is a partially cut-away plan view of the padded splint in the flat, unformed condition, showing, principally in broken lines, a thin, flat malleable metal splint member encased in a padded covering; and FIG. 8 is a transverse cross sectional view taken along line 8—8 of FIG. 7 showing features of the padded splint and showing in phantom lines outboard regions of the metal splint bent upwardly to conform to a right hand wrist and, alternatively, bent downwardly to conform to a left hand wrist.

In the various FIGS. identical elements and features are given the same reference numbers.

DESCRIPTION OF THE PREFERRED EMBODIMENT

Figure 1:
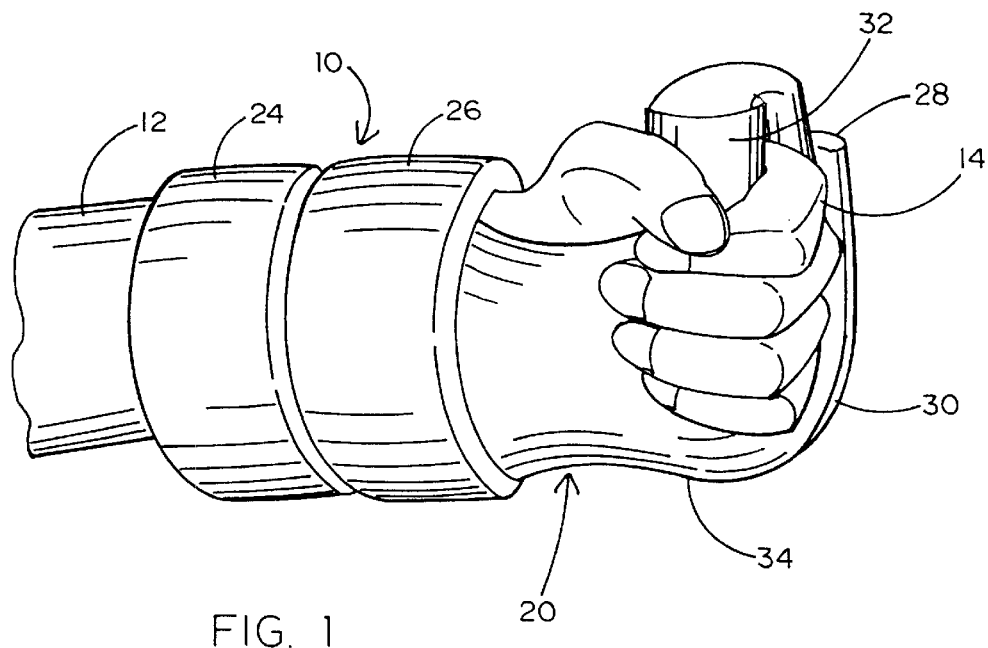
FIG. 1 is a perspective drawing showing a universal hand orthotic device in accordance with the present invention, an attaching mitt portion being shown, by way of illustrative example, detachably attached to an individual's left hand and wrist and a representative hand bolster detachably attached to a hand-gripping region of a mitt portion of the device.

There is shown in FIG. 1, a universal hand orthotic device 10 in accordance with the present invention. Universal hand orthotic device 10 is easily adaptable (as more particularly described below) for use on either a left hand or a right hand of a wide range of sizes to treat contractures due to immobility.

For descriptive purposes, with no limitation being intended or implied, device 10 is depicted in FIG. 1 installed on an individual's left wrist (including the lower forearm) 12 and left hand 14 for treating contractures of the individual's left hand (including the fingers thereof).

Figure 2:
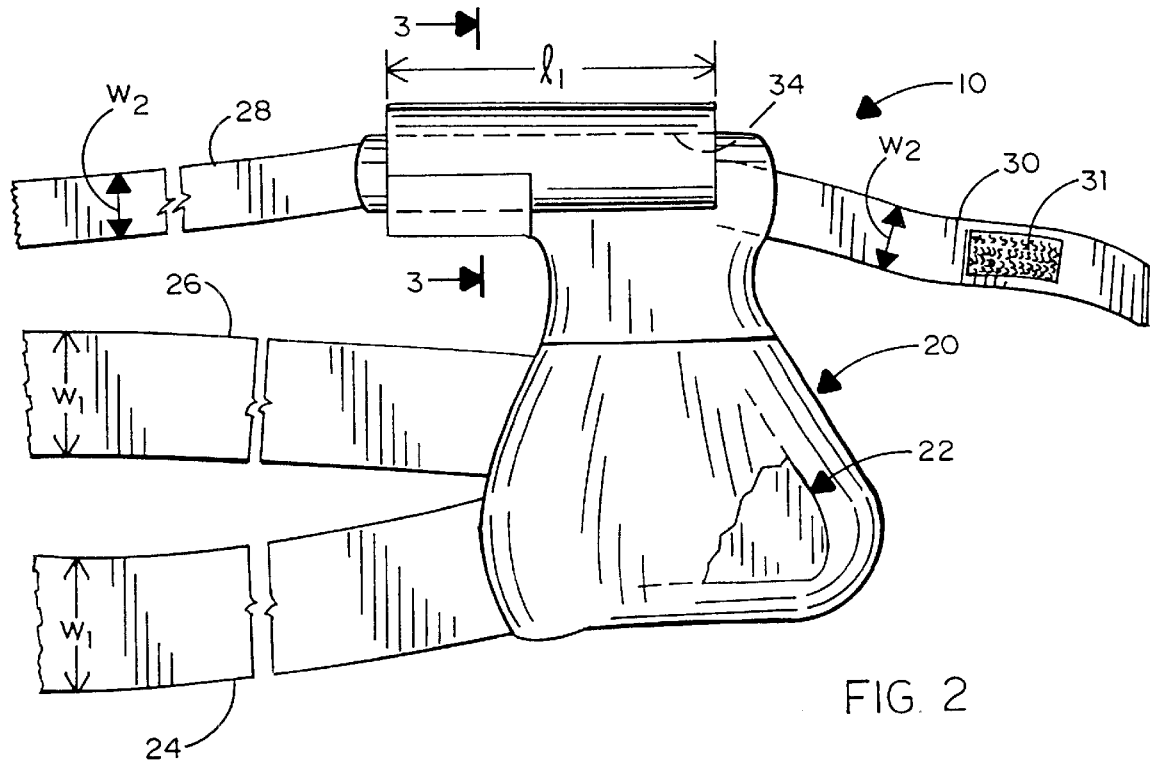
FIG. 2 is a partially cutaway plan view of the orthotic device of FIG. 1, showing the device of FIG. 1 in an unformed, flat condition, showing part of a padded splint installed in the mitt portion and showing four attachment straps fixed to the mitt portion.

Universal hand orthotic device 10, which is shown in FIG. 2 its flat, pre-installation condition, comprises generally a soft, padded envelope or mitt 20 in which a splint member 22 is received. A plurality (four) of soft, elongate, padded fabric attachment straps 24, 26, 28 and 30 are preferably fixed to different regions of mitt 20, as by being sewn thereto. Although four such attachment straps (24, 26, 28 and 30) are depicted, more or fewer straps may be provided. As shown in FIGS. 1 and 2, attachment straps 24 and 26 are located at generally right angles to lower regions of mitt 20 for attaching device 10 to a users wrist area, and attachment straps 28 and 30 are located at uppermost regions of the mitt for attaching device 10 to the user's hand.

Conventional "hook and loop" pairs enable releasable securing of attachment straps 24–30 to a patients wrist and hand. Accordingly, straps 24, 26, 28 and 30 include conventional "hook" strips, for example, strip 31 shown on strap 30, for enabling mitt 20 of device 10 to be firmly, but easily, detachably attached to an individual's wrist and hand, as depicted in FIG. 1 for left wrist 12 and left hand 14. Attachment straps 24–30 are each constructed of a durable knit fabric (such as polyester) that is soft against a users skin and that functions along its entire length as a "loop" region to which the corresponding "hook" strip (for example, attachment strip 28 and corresponding hook strip 31) detachably hooks anywhere along the strap. Such hook and loop attachment strap securing enables straps 24–30, in the aggregate, the securely attach device 10 to a user's wrist and hand (for example left wrist 12 and left hand 14, as shown in FIG. 1.

Attachment straps 24–30 are made sufficiently long to enable attachment of device 10 to most sizes of wrists and hands of adults—the segment of the population most likely to require treatment of hand and finger contractures due to immobility. By way of illustrative example, attachment straps 24 and 26 used for attaching device 10 to a wrist may each be about 15 inches ling and have a width, $w_1$, of about 1.5 to about 2 inches (FIG. 2). Straps 28 and 30 may each be about 6 inches long and have a width, $w_2$, of about 1 inch.

Shown included as part of device 10 is a generally cylindrical, firm, yet somewhat pliant, bolster 32 that is configured for being removably installed onto a sidewardly extending, hand gripping region 34 (shown in broken lines in FIG. 2) of mitt 20.

Figure 3:
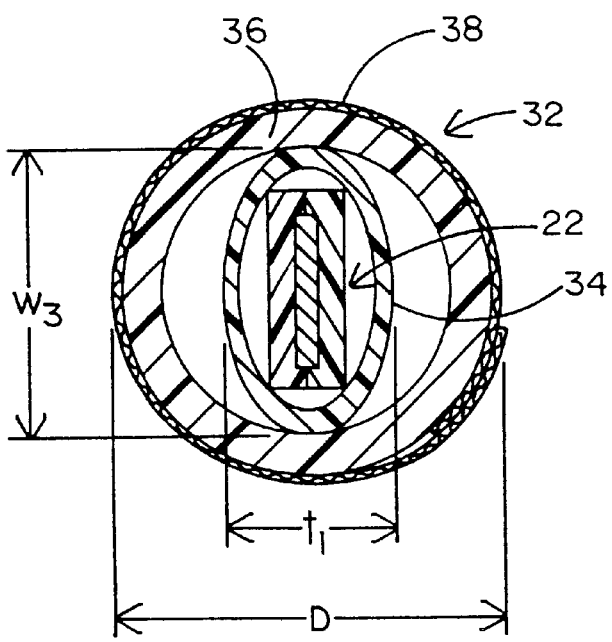
FIG. 3 is a transverse cross sectional view taken along line 3—3 of FIG. 2 showing the hand bolster installed on a hand-gripping region of the mitt portion of the device.

As depicted in FIG. 3, bolster 32 comprises a flexible, split, closed-cell plastic foam tube 36 covered by a soft, non-skin irritating fabric layer 38. When opened, split tube 36 fits over and partially around hand gripping region 34, being held in place, for example, by a strip of hook and loop fasteners.

By way of example, hand-gripping region 34 may have a width, $w_3$, of about 1.5 inches and a thickness, $t_1$, of about 0.5 inches. Bolster 32 may have a length, $l_1$ (FIG. 2) of about 4.5 inches, and when installed onto hand-gripping portion 34 may provide a generally round finger grip, having a diameter, D (FIG. 3), of about 1.75 inches.

Figure 4:
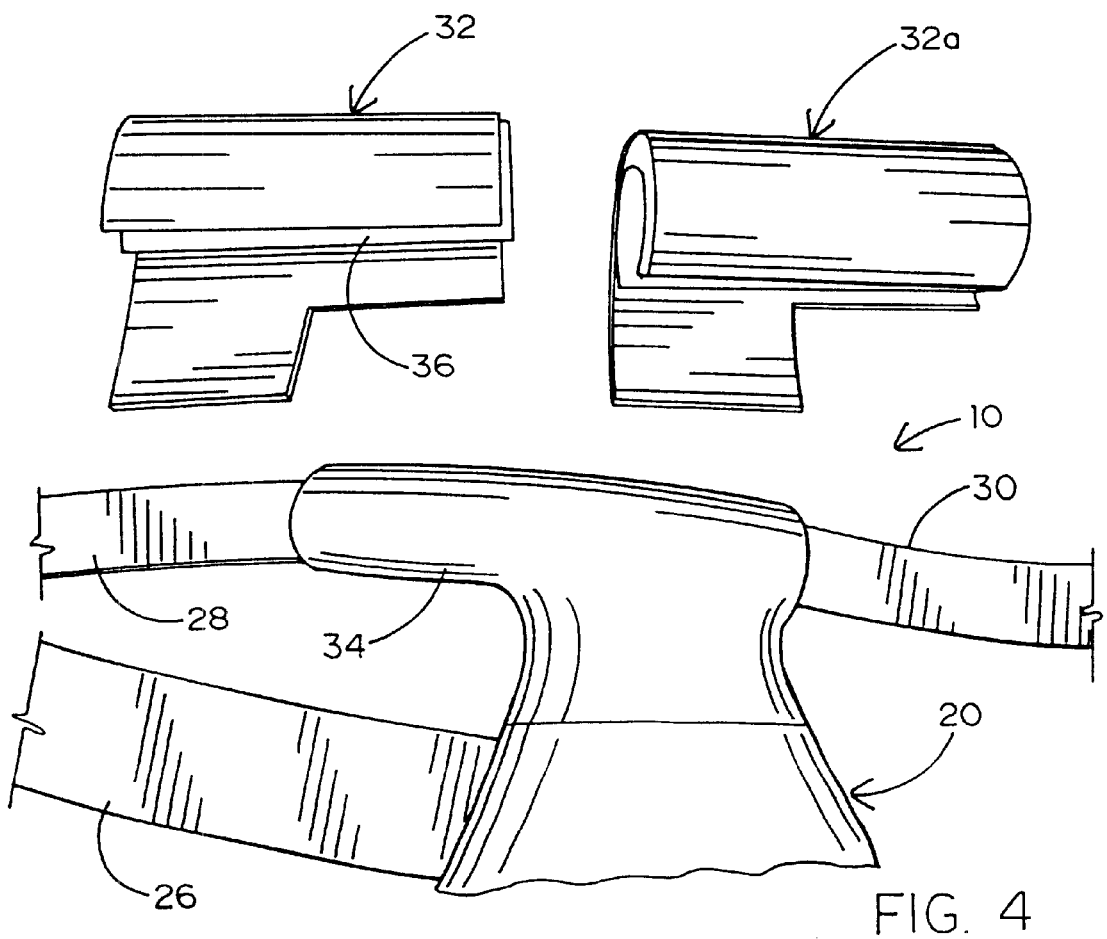
FIG. 4 is a partial plan view, similar to FIG. 2, of the unformed orthotic device, showing two representative hand bolsters of different diameters detached from the hand-gripping region of the mitt portion.

As shown in FIG. 4, device 10 preferably includes, in addition to above-described bolster 32, at least one additional bolster 32a of somewhat larger installed diameter, for example, of about 2.25 inches. Be installing a succession of bolsters 32, 32a and so forth of increasing diameters on mitt region 34, the fingers of a wearer's hand are gradually caused or enabled to be opened to their full range of motion. "Hook and loop" pairs (not shown) detachably secure bolsters 32, 32b and all other bolsters to mitt region 34.

Mitt 20 is preferably covered with a soft fabric, at least upper hand receiving regions around finger region 34 being covered with a comfortable, non-skin irritating knit fabric, such as polyester.

Figure 5:
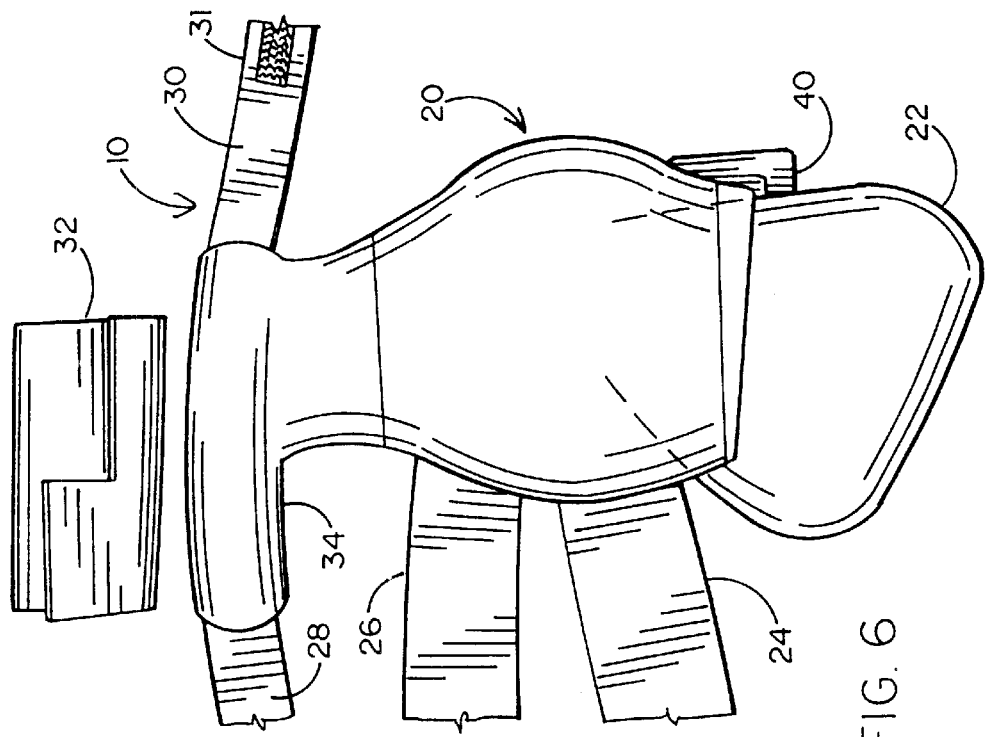
FIG. 5 is a plan view similar to FIG. 2, showing the hand bolster removed from the mitt portion, showing the padded splint separate from and along side the mitt portion, and also showing a lower region of the mitt portion open for enabling the removal and insertion of the padded splint.
Figure 6:
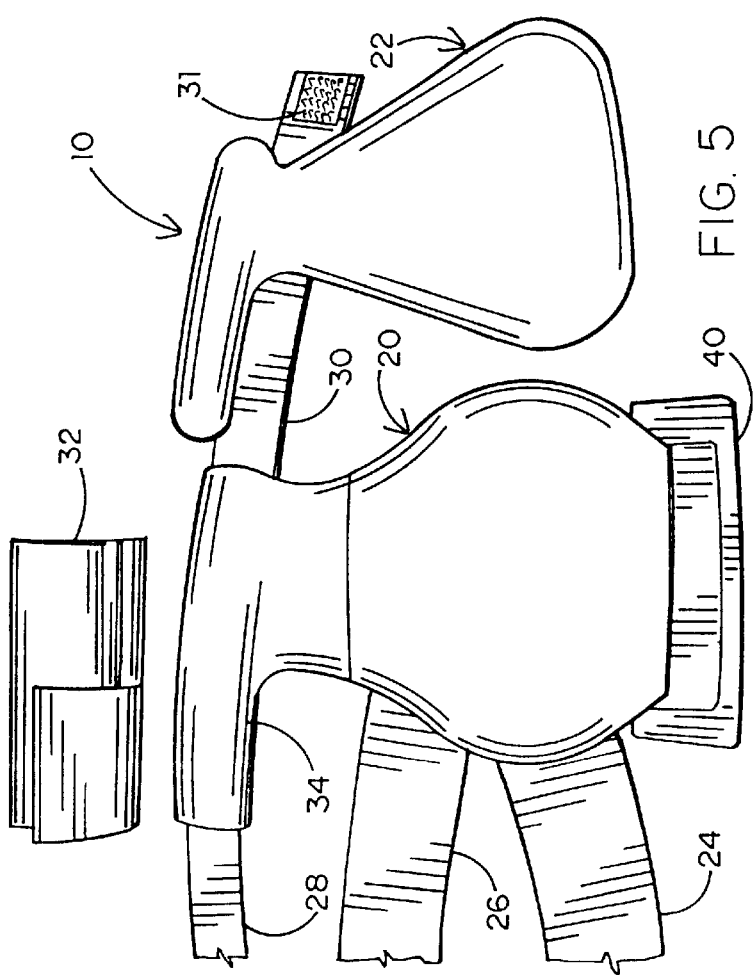
FIG. 6 is a plan view similar to FIG. 5, showing the padded splint partially inserted into the mitt portion of the device.

FIG. 5 depicts padded splint 22 removed from, and along one side of, mitt 20. Padded splint 22, more particularly described below, has the same general flat shape as mitt 20 and is sized to fit snugly inside the mitt. A lower end region 40 of mitt 20 is shown opened up so that padded splint 22 can be installed into the mitt (the mitt lower end region is closed in use by "hook and loop" pairs (not shown). In FIG. 6, padded splint 22 is shown partially installed in mitt 20 through open mitt lower end region 40.

Padded splint 22 is shown in greater detail in FIGS. 7 and 8. Shown comprising padded splint 22 is a manually bendable metal splint member 42 covered by a first, thin upper soft plastic pad 44 and a second, thin lower soft plastic pad 46. Each of pads 44 and 46 preferably has a thickness, $t_2$, of about 0.188 inches and may have inner regions cut out to provide for splint member 42. Alternatively, pads 44 and 46 may be formed of two or more layers with the abutting inner layers having a cutout to receive splint member 42. In either case, padded splint 22 preferably has an overall thickness $t_3$, of about 0.375 inches. Upon assembly of padded splint 22, upper and lower pads 44 and 46 are cemented together and to splint member 42 to form a composite structure (FIG. 8).

Splint member 42 is formed having an elongate central shaft or wrist support region 50 that is bisected by a longitudinal axis 52 and that has a preferred width, $w_4$, of about 1 inch. Length, $L_1$, of splint member 42 along longitudinal axis 52 is preferably between about 7 and 7.5 inches. Projecting sidewardly (towards the left as shown in FIG. 7) from an upper end of shaft region 50 is a hand support or finger region 54. A longitudinal axis 56 of finger region 54 is preferably at an angle, α, of about 75 to about 80 degrees, and more preferably about 77 degrees, relative to shaft region axis 52 Preferably finger portion 54 has a length, $L_2$, along finger region axis 56 of about 3.25 inches, and has a preferred width, $w_5$, of about 0.5 inches. A short stub region 58, having a length, $L_3$, of only about 1 inch, extends along finger region axis 56 in a direction opposite to that of finger region 54.

As is evident from FIG. 7, a lower region of splint member 42 is, in appearance, shaped somewhat like a ship's anchor with sidewardly extending left and right ears 59 and 60, having, respectively, an enlarged left side region 61 and an enlarged right side region 62. Side regions 61 and 62 are symmetrical with respect to shaft region axis 52.

Left side region 61 is connected to shaft region 50 by a short connection region 64 having a width, $w_6$, of about 0.5 to about 0.75 inches, 0.75 inches being more preferred. In a similar manner, right ride region 62 is connected to shaft region 50 by a short connection region 66 also having a width, $w_6$, of about 0.75 inches.

A longitudinal axis 68 of left side region 61 is separated from a longitudinal axis 70 of right side region 62 by a distance, $d_1$, of about 3 inches. Longitudinal side region axes 68 and 70 are parallel to one another and to shaft region axis 52. Overall height, h, of left and right side regions 61 and 62, is about 2.25 inches. A curved outer edge 72 of left side region 61 is spaced a distance, $d_2$, of about 2.25 inches from shaft region axis 52. Similarly, a curved outer edge 74 of right side region 62 is spaced a distance, $d_2$, of about 2.25 inches from shaft region axis 52. Each of left and right side regions 61 and 62 has a maximum width, $w_7$, of about 1.25 inches.

As also shown in FIG. 7, lower regions of pads 44 and 46 are generally triangular in shape and provide a minimum edge distance $d_3$, of about 0.25 to about 0.375 inches relative to splint side regions 61 and 62, as well as to finger and stub regions 54 and 56. Device mitt 20 (as depicted in FIG. 6) is shaped and sized to closely encase or fit over padded splint 22.

Splint member 42 is formed from a flat sheet of a stiff, yet manually bendable or formable material, preferably aluminum (such as type 5052 or 6061), having a thickness, $t_4$, between about 0.040 and about 0.0938 inch, with 0.040 inch being preferred (FIG. 8).

It is, however, to be understood that the foregoing dimensions of splint member 42 are given merely for illustrative purposes and are considered appropriate for device 10 constructed for use with a normal, grown person's left or right hand. A proportionally smaller splint member 42 and padded splint 22 may, for example, be provided for a corresponding device 10 intended for use on a child's or small woman's hand.

A key feature and important advantage of padded splint 22 is its ability to be manually conformed to fit either a patient's left or right wrist region as the need for treatment of either the patient's left or right hand by orthotic device 10 requires. Left and right side regions 61 and 62 of splint member 42 can thus be manually bent upwardly in the direction of Arrows "A" (FIG. 8) to conform padded splint 22 (and hence mitt 20—not shown-in which the padded splint is received) to a patient's left wrist region 12 (shown in phantom lines). Contrariwise, left and right side regions 61 and 62 of splint member 42 can thus be manually bent downwardly in the direction of Arrows "B" (FIG. 8) to conform padded splint 22 (and hence mitt 20—not shown-in which the padded splint is received) to a patient's right wrist region 12 (not shown).

Moreover, splint member shaft region 50 and finger region 54 can be manually bent and/or twisted as may be needed to further conform padded splint 22 and mitt 20 to a particular patient's left or right hand, as the case may be, before and during treatment.

In addition, after device 10 has been conformed for use on one hand of a patient, it can be readily re-conformed for use on the patient's other hand if treatment of the other hand is needed. When suitably sanitized and if permitted by the governing or regulating health organization, device 10 can be re-conformed in the above-described manner for reuse on different patients with different hand and wrist sizes.

Although there has been described and illustrated a universal hand orthotic device for use on either a patient's left hand or right hand for treating contractures of the hand and/or fingers in accordance with the present invention for purposes of illustrating the manner in which the invention may be used to advantage, it is to be appreciated that the invention is not limited thereto. Therefore, any and all variations and modifications that may occur to those skilled in the applicable art are to be considered as being within the scope and spirit of the claims as appended hereto.

What is claimed is:

1. A universal orthotic device for treating contractures of either a patient's left hand or right hand, said universal hand orthotic device comprising:
   a. a manually bendable single piece solid, flat splint element having an elongate central, wrist support region with an elongate slender hand support region projecting sidewardly from an upper end of said central region at an angle, α, of between about 75 and 80 degrees relative to a longitudinal axis of said central region, a first ear projecting outwardly relative to said longitudinal axis to one side of a lower end of said central region and a second ear projecting outwardly relative to said longitudinal axis to an opposite side of the lower end of said central region, said first and second ears being manually bendable relative to said central region to configure said splint element to fit at least partially around either a patient's left wrist or a patient's right wrist according to the intended use of said device;

b. a padded fabric mitt configured for receiving said splint element, said mitt having a hand region and including closure means for retaining the splint element in the mitt; and c. at least one strap attached to said fabric mitt for enabling the releasable attachment of the mitt to a patient's wrist and hand.

2. The universal hand orthotic device as claimed in claim 1, wherein said splint element is constructed from a relatively soft aluminum alloy having a sheet thickness of between about 0.040 and about 0.0938 inches.

3. The universal hand orthotic device as claimed in claim 1, wherein said angle, α, is about 77 degrees.

4. The universal hand orthotic device as claimed in claim 1, wherein said central region has a width of about one inch.

5. The universal hand orthotic device as claimed in claim 1, wherein said hand support region has a width of about 0.5 inches.

6. The universal hand orthotic device as claimed in claim 1, wherein each of said first and second ears extend about 2.25 inches outwardly from the longitudinal axis of said central region.

7. The universal hand orthotic device as claimed in claim 1, wherein the overall height of said splint element is between about 7 and about 7.5 inches along said central region longitudinal axis.

8. The universal hand orthotic device as claimed in claim 1, wherein said first and second ears each include an enlarged outboard end region joined to said central region by a smaller, necked-down region.

9. The universal hand orthotic device as claimed in claim 8, wherein said necked-down region has a width parallel to said central region longitudinal axis of between about 0.5 and about 0.75 inches.

10. The universal hand orthotic device as claimed in claim 1, including first and second, relatively soft pads, said splint element being disposed between said first and second pads to thereby form a padded splint assembly, said mitt being configured for receiving said padded splint assembly.

11. The universal hand orthotic device as claimed in claim 10, wherein said first and second pads are contoured to generally follow the shape of the splint element.

12. The universal hand orthotic device as claimed in claim 10, wherein each of said first and second pads are formed from a closed cell plastic foam material.

13. The universal hand orthotic device as claimed in claim 12, wherein said padded splint assembly has a combined thickness of about 0.375 inches.

14. The universal hand orthotic device as claimed in claim 10, wherein said first and second pads are cemented together around said splint element.

15. The universal hand orthotic device as claimed in claim 1, wherein the exterior of said mitt hand region is formed of a smooth, non-skin irritating fabric.

16. The universal hand orthotic device as claimed in claim 1, including at least one resilient cylinder configured for detachable attachment to a finger-grip region of said mitt.

17. A universal hand orthotic device for treating contractures in either a patient's left hand or right hand, said universal hand orthotic device comprising:

a. a bendable solid, flat splint element formed having an elongate central, wrist support region with an elongate hand support region projecting sidewardly from an upper end of said central region at an angle between about 75 and about 80 degrees, relative to a longitudinal axis of said central region, a first ear projecting outwardly relative to said longitudinal axis to one side of a lower end of said central region and a second ear projecting outwardly relative to said longitudinal axis to an opposite side of the lower end of said central region, said first and second ears each including an enlarged outboard end region joined to said central region by a necked-down region having a width parallel to said central region longitudinal axis of between about 0.5 inch and about 0.75 inch, and each being manually bendable relative to said central region to configure said splint element to fit at least partially around either a patient's left wrist or a patient's right wrist according to the intended use of said device;

b. first and second, relatively soft flat pads, said splint element being disposed between said first and second pads to thereby form a padded splint assembly, said first and second pads being contoured to generally follow the shape of the splint element;

c. a padded fabric mitt configured for receiving said padded splint assembly, said mitt having a hand region and including closure means for retaining the padded splint assembly in the mitt; and d. at least one strap attached to said fabric mitt for enabling the releasable attachment of the mitt to a patient's wrist and hand.

18. The universal hand orthotic device as claimed in claim 17, wherein said splint element is substantially planar in shape before any bending of said first and second ears, and is constructed from a relatively soft aluminum alloy having a sheet thickness of between about 0.040 and about 0.0938 inches.

19. The universal hand orthotic device as claimed in claim 17, wherein said splint element has an overall height between about 7 inches along said central region longitudinal axis, wherein said splint element central region has a width of about one inch, wherein said splint element hand support region has a width of about 0.5 inches and wherein each of said first and second ears extend about 2.25 inches from the longitudinal axis of said central region.

20. The universal hand orthotic device as claimed in claim 17, wherein each of said first and second pads are formed from a closed cell plastic foam material having a thickness of about 0.188 inches and are cemented together around said splint element to form a padded splint assembly having a thickness of about 0.375 inches.

21. The universal hand orthotic device as claimed in claim 17, wherein the exterior of said mitt hand region is formed of a smooth, non skin irritating fabric.

22. The universal hand orthotic device as claimed in claim 17, including at least one resilient cylinder configured for detachable attachment to a finger-grip region of said mitt.

23. A universal hand orthotic device for treating contractures in either of a patient's left hand or right hand, said universal hand orthotic device comprising:

a. a solid, one piece, flat manually bendable splint element formed having an elongate central, wrist support region with an elongate hand support region projecting sidewardly from an upper end of said central region at an angle between about 75 and about 80 degrees, relative to a longitudinal axis of said central region, a first ear projecting outwardly relative to said longitudinal axis to one side of a lower end of said central region and a second ear projecting outwardly relative to said longitudinal axis to an opposite side of the lower end of said central region, said first and second ears each including an enlarged outboard end region joined to said central region by a necked-down region and each being manually bendable relative to said central region to configure said splint element to fit at least partially around either a patient's left wrist or a patient's right wrist according to the intended use of said device;

b. first and second, relatively soft flat pads constructed from a closed cell plastic foam material having a thickness of at least about 0.188 inches, said splint element being disposed between said first and second pads to thereby form a padded splint assembly, said first and second pads being contoured to generally follow the shape of the splint element and being cemented together around said splint element;

c. a padded fabric mitt configured for receiving said padded splint assembly, said mitt having a hand region and including closure means for retaining the padded splint assembly in the mitt, the exterior of said mitt hand region being formed of a smooth, non skin irritating fabric;

d. at least two straps attached to said fabric mitt for enabling the releasable attachment of the mitt to a patient's wrist and hand; and e. a plurality of resilient cylinders of increasing diameters configured for detachable attachment to a finger grip region of said mitt.

24. The universal hand orthotic device as claimed in claim 23, wherein said splint element is substantially planar in shape before any bending of said first and second ears, and is constructed from a relatively soft aluminum alloy having a sheet thickness of between about 0.040 and about 0.0938 inches.

25. The universal hand orthotic device as claimed in claim 23, wherein said splint element has an overall height between about 7 inches and about 7.5 inches along said central region longitudinal axis, wherein said splint element central region has a width of about one inch, wherein said splint element hand support region has a width of about 0.5 inches and wherein each of said first and second ears extend about 2.25 inches from the longitudinal axis of said central region.

26. The universal hand orthotic device as claimed in claim 23, wherein said necked-down region has a width parallel to said central region longitudinal axis of between about 0.5 and about 0.75 inches.

* * * * *